US007867762B2

(12) United States Patent
Stahl et al.

(10) Patent No.: US 7,867,762 B2
(45) Date of Patent: Jan. 11, 2011

(54) CLIMATE CONTROL UNIT WITH GERM-PROOF SEPARATED SECTIONS

(75) Inventors: Hermann Stahl, Nidderau-Ostheim (DE); Olaf Broemsen, Moerfelden-Walldorf (DE); Ulrike Hohenthanner, Hanau (DE); Rainer Schuck, Im Neufeld 1 (DE); Waldemar Pieczarek, Bruchkoebel (DE)

(73) Assignee: Thermo Electron Led GmbH, Langenselbold (DE)

( * ) Notice: Subject to any disclaimer, the term of this patent is extended or adjusted under 35 U.S.C. 154(b) by 997 days.

(21) Appl. No.: 11/029,630

(22) Filed: Jan. 6, 2005

(65) Prior Publication Data
US 2005/0244306 A1 Nov. 3, 2005

(30) Foreign Application Priority Data
Jan. 6, 2004 (DE) ................... 10 2004 001 104

(51) Int. Cl.
*C12M 1/00* (2006.01)
*C12M 3/00* (2006.01)
(52) U.S. Cl. ................. 435/303.1; 435/243; 435/303.2; 600/22
(58) Field of Classification Search .......... 435/243, 435/303.1, 303.2, 809; 219/407; 119/218, 119/311, 317, 320; 600/22
See application file for complete search history.

(56) References Cited

U.S. PATENT DOCUMENTS

| 4,121,571 | A | * | 10/1978 | Pickering | ................... 600/22 |
|---|---|---|---|---|---|
| 4,336,329 | A | | 6/1982 | Hesse et al. | |
| 4,622,049 | A | | 11/1986 | Abernathy et al. | |
| 4,923,816 | A | * | 5/1990 | Heeg et al. | ............... 435/303.2 |
| 5,190,879 | A | * | 3/1993 | Wolfe et al. | ............... 435/297.1 |
| 5,519,188 | A | * | 5/1996 | Yuichi et al. | ................ 219/407 |
| 5,858,770 | A | | 1/1999 | Perlman | |
| 5,890,703 | A | | 4/1999 | Kaus et al. | |
| 5,908,776 | A | | 6/1999 | Burbaum et al. | ......... 435/288.3 |
| 6,518,059 | B1 | | 2/2003 | Butts | ....................... 435/303.1 |
| 6,673,595 | B2 | * | 1/2004 | Barbera-Guillem | ...... 435/286.2 |
| 2003/0040104 | A1 | * | 2/2003 | Barbera-Guillem | ...... 435/286.2 |
| 2005/0084420 | A1 | * | 4/2005 | Osawa et al. | .................. 422/99 |

FOREIGN PATENT DOCUMENTS

| DE | 1914585 | 3/1969 |
|---|---|---|
| DE | 19536373 C1 | 9/1995 |
| DE | 20022783 U1 | 2/2000 |
| JP | 2004154099 | 3/2004 |
| WO | WO 98/30676 | 7/1998 |

* cited by examiner

*Primary Examiner*—William H Beisner
*Assistant Examiner*—Michael Hobbs

(57) ABSTRACT

Climate control unit with an interior section containing a storage space and with a closable access opening to the storage section whereby at least one part of the interior section is separated and sealed against the rest of the interior section thus forming a separate germ-proof section. The division takes place at least in part by a membrane that is permeable for water vapor and gas but impermeable for microorganisms.

27 Claims, 4 Drawing Sheets

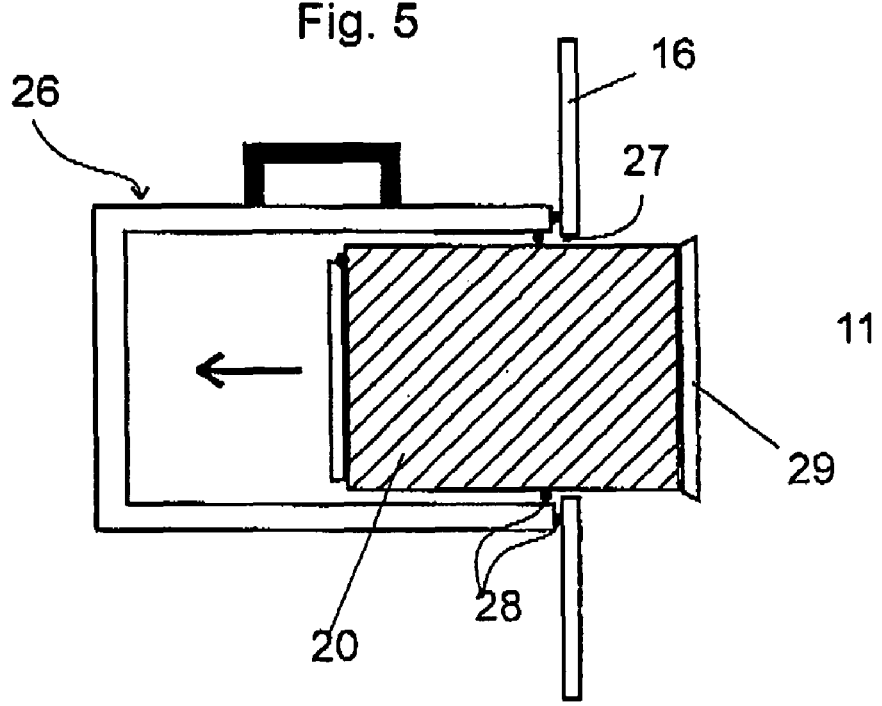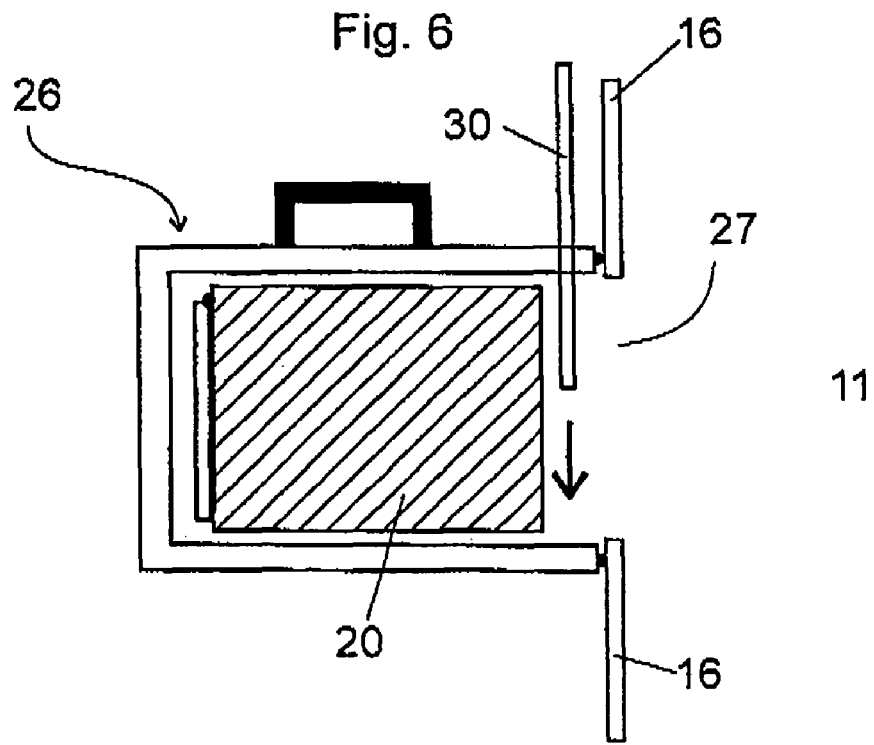

US 7,867,762 B2

CLIMATE CONTROL UNIT WITH GERM-PROOF SEPARATED SECTIONS

CROSS REFERENCE TO RELATED APPLICATIONS

This application claims priority to German Patent Application Serial No. 102004001104.4, filed Jan. 6, 2004, titled CLIMATE CONTROL UNIT WITH GERM-PROOF SEPARATED SECTIONS, the disclosure of which is incorporated herein by reference in its entirety.

FIELD OF THE INVENTION

The invention concerns a climate control unit with an internal section containing a storage section and with a closable access opening to the storage section and also a membrane box for application in such a climate control unit.

BACKGROUND OF THE INVENTION

A climate control unit is a laboratory apparatus for the storage of predominantly biological or chemical specimens in definite climatic conditions. Examples of this are incubators and cooling or freezing units. Such climate control units have a storage section that is enclosed by a housing making it gastight and thermally isolated. The storage section is accessible via an opening that frequently takes up the entire front side of the climate control unit and that can be closed with a closing device so that it is gastight. Usually the storage section is provided with horizontal inserts for storing the specimens. Climate control units of such type offer in their storage section a climate with predetermined temperature and air moisture and also a predetermined $CO_2$ concentration in the case of incubators. The closing device is often an external swing door behind which usually a transparent inner door is arranged as a gas screen. This transparent inner door prevents a fast gas exchange from taking place between the storage section and the surroundings when the external swing door is opened. At the same time the transparent gas screen allows the view of the samples. So opening times of the gas screen can be reduced to a minimum, thus largely avoiding unnecessary disturbances in the storage section climate. In order to further reduce disturbances, divided enclosures and partitioned gas screens are known. For example, there are gas screens with six separate access openings each of which is closable by its own door. Such partitioned gas screens make it possible to access definite enclosures and storage cells whereby the other storage cells stay protected.

A prevalent method for the humidification of the atmosphere of an incubator takes place via passive evaporation of water in an open water bath (water bath). While the advantage is a very homogenous distribution of moisture in the air, the disadvantage is the open water surface. Dirt particles, viruses, fungi, bacteria and mycoplasma grow in the water bath in great quantity once they have entered into the water through drops or dust.

A risk of contamination exists for the specimens also through other specimens. On the one hand the specimens can be infested with foreign germs such as fungi or bacteria. On the other hand even the specimens themselves can be dangerous agents. This can mean a risk for other specimens through cross-contamination and also for the operating person. If the storage section of the climate control unit is contaminated, mostly an expensive disinfection of the entire equipment is required resulting in long down times.

For the prevention of contamination and cross-contamination membrane pouches made out of germ-proof membrane are known. Individual specimen carriers can be packed and sealed in such membrane pouches and stored in a climate control unit. However the handling of these membrane pouches is considered to be inconvenient. Accordingly they find a low level of acceptance among users.

With this background the task underlying the present invention is to specify a climate control unit that reduces the risk of contamination of the entire equipment and of cross-contamination and is user-friendly in spite of that.

SUMMARY OF THE INVENTION

A climate control unit in accordance with claim 1 thus has an interior section containing a storage section and a closable access opening to the storage section whereby at least one part of the interior section is separated from the rest of the interior section, making it germ-proof. Thus germ-proof separated section is formed. The separation is made possible at least partly by a membrane that is permeable for water vapor and gas but impermeable for microorganisms.

The advantage as opposed to the prior art lies in the fact that an acute contamination in one part of the interior section cannot encroach upon the other parts of the interior section. A cross-contamination between different germ-proof separate parts is not possible. Therefore in case of a contamination, the whole interior section does not need to be disinfected, instead only a sub area.

The germ-proof separation takes place at least partly via a membrane that is permeable for water vapor and gas, but impermeable for microorganisms. The permeability of the membrane is determined by its pores. The pores must be sufficiently big so that water vapor and gas can penetrate the membrane unobstructed as far as possible. On the other hand the size of the pores should be restrictive in such a manner that even the smallest microorganisms cannot penetrate the pores. Preferentially the membrane therefore has pores whose maximum size is 0.5 µm. and a particularly preferable pore size that is smaller than 0.2 µm.

The climate control unit can be an equipment that controls only the temperature of the interior section like a cooling or freezing unit. Preferentially the climate control unit is an equipment that additionally allows the adjustment of the atmosphere in the storage section like an incubator.

In an advantageous design variant the climate control unit has a gas screen between the access opening and the interior of the climate control unit. The gas screen closes the interior section of the climate control unit. The use of the gas screen both as a swing door and also a gas screen that can be pulled out on rails can be advantageous. A partitioned gas screen with several openings is particularly preferential. Several openings allow access to individual compartments in the climate control unit with minimum disturbance to the atmosphere in the remaining compartments.

Through germ-proof separation of individual sections in the interior section of the climate control unit by means of a membrane, disturbances of the atmosphere are further reduced. The membrane is preferentially stretched over a frame and mounted on it. In another variant of the invention the frame is attached inside the climate control unit and equipped with a sealing mechanism so that it is sealed off from one or several interior walls of the climate control unit. In this manner e.g., a tray on the floor or a dent in an interior wall of the climate control unit is covered with a membrane and separated from the remaining interior section, making it germ-proof. Depending on the purpose of application, the frame can be set in the force fit with a flexible sealing in the inner housing of the climate control unit or it can be mounted permanently. Also a sealing with other current methods e.g., with silicon sealing and gravitational force or compression by bolt force is possible.

In an advantageous design form of the climate control unit, electric components such as motors or ventilators and sensors are accommodated in such a germ-proof and separated section for protection against contamination. It is particularly advantageous if a water bath provided for the humidification of the storage section is protected in this manner by a membrane. Since the membrane is permeable for gas and water vapor moisture can diffuse into the entire storage section. This is particularly supported if the water bath is tempered and if additionally a ventilator is provided in the separated section that promotes the diffusion of the moist air. It is also possible to rinse the moist air by means of a ventilator through a membrane tube that is led through the storage section and thus provides for even moisture in the storage section.

Fumigation of the specimens can increase the moisture in the storage section. Therefore in a preferential design form of the climate control unit a heat bridge (cold spot) is attached between the separated section with the water bath and the storage section. Excess moisture in the storage section condenses on it and can be led back into the water reservoir.

In another preferential design form a part of the storage section is separated by a membrane box thus making it germ-proof. The membrane box is enclosed by walls making it germ-proof, whereby at least one part of the wall surfaces consists of membrane. The membrane should be measured such that a sufficient exchange of gas and moisture can take place. In general it is sufficient if e.g., only one sidewall is made out of membrane and the rest of the walls out of gastight material. A membrane box offers space for one or several specimen containers. The climate control unit can in turn have either one or several membrane boxes. In the extreme case one membrane box takes up the entire storage section of the climate control unit. In case of several membrane boxes, it is essential that they do not cover the membranes in a two-way manner so that the diffusion of gas and moisture is not obstructed. Therefore it is meaningful not to fill out the entire storage section of the climate control unit with membrane boxes instead to let intermediate sections free so that the diffusion can take place without obstruction. In order to further improve the diffusion, the air exchange in the storage section can be increased e.g., by arrangement of ventilators.

It is particularly preferential to divide the entire storage section of the climate control unit by membrane boxes. A cross-contamination between the individual boxes is not possible. In case of contamination in one membrane box, the concerned box can be replaced and disinfected individually or destroyed. A further advantage lies in the fact that the air moisture in the climate control unit in accordance with the invention can be increased as opposed to devices of prior art. The risk of contamination through condensed water is strongly reduced by the membrane partitions. A higher moisture level offers better protection from the withering of the specimens.

The individual membrane boxes can be mounted permanently in the climate control unit. It is preferable to releasably attach them in the interior section of the climate control unit with a fixing device. In the interior section of the climate control unit e.g., a base frame or a frame can be provided in which several membrane boxes are inserted. Also a pullout mechanism of the type of drawers is possible. Hanging the membrane boxes in the inner space can be particularly advantageous, besides also saving material. It is also useful if the membrane box is fastened to one or several interior walls of the climate control unit.

In a variant of the design form of the invention the membrane box is releasably fastened to the gas screen of the climate control unit. Thus it can be inserted from the front into an opening of the closed gas screen and can be fastened with a quick-release fastener. In another variant the membrane box is permanently mounted on the reverse side of the gas screen. Then the membrane box can be folded or pulled from the interior section of the climate control unit when the gas screen is opened. In this case the membrane box is sealed against the gas screen on the front side via a sealing. The gas screen then forms the front wall of the membrane box.

It is advantageous that the membrane box has at least one opening for the loading and unloading of specimens. The opening is releasably closable with a closing device that thus makes it germ-proof. Preferentially this closing device consists of a door. Other variants are membrane parts that are put on top of each other or also a screw closure. It is meaningful if the membrane box has such an opening for loading at the front side and at the reverse side. The membrane box can then be inserted into the climate control unit with any of the sides at the front.

When the membrane box is sealed at the front side from the gas screen it is particularly advantageous if a closing device is integrated into the gas screen. Thereby the membrane box can either be fastened in the interior section of the climate control unit, e.g., on a frame or a base frame, and can be sealed against the gas screen at its open front side via a flexible sealing. Spring systems are useful for increasing the surface pressure. The inner space of the membrane box is accessible via a door integrated into the gas screen in this design form. In its cross section, the door is then purposefully smaller than the cross section of the membrane box, with which this is sealed to the gas screen. The advantage of such a design form lies in its easy usability. Each membrane box is directly accessible via a door in the gas screen.

In another preferential variant the closing device is directly fastened to the membrane box. This makes it possible for the whole membrane box to be pulled out of the climate control unit in its germ-proof and closed state. Thus specimens can be transported in germ-proof surroundings from one equipment to other equipments e.g., in vacuum cupboards, drying cupboards or microbiological safety cabinets. Such a membrane box is purposefully pushed from the front into a gas screen. A gas screen must have openings for it that are adjusted to the cross-section of the membrane boxes. If a membrane box was pulled out of the gas screen the resulting aperture can be covered with a substitute closing device. This is also possible by an automatic mechanism.

The task of the invention is also solved by a membrane box for application in a climate control unit whereby the membrane box is enclosed by walls making it germ-proof and at least one sub area of these walls is formed by a membrane. The membrane is permeable for gas and water vapor but impermeable for microorganisms. The membrane box has at least one load opening that can be releasably closed to make it germ-proof via a closing device, particularly a door. As described above the closing device can also consist of membrane parts or a screw closure. It is useful if the load opening is aligned with the access opening of the climate control unit. The closing device can also be connected functionally to the access opening of the climate control unit.

It is mostly sufficient if the membrane box has only one membrane window and otherwise has a gastight formation. For the gastight closure of the membrane box it is then sufficient if the membrane window is covered thus making it gastight. The membrane box can also have a closable form.

Preferentially the membrane has pores with a maximum size of 0.5 μm. A pore size smaller than 0.2 μm is particularly advantageous.

In a preferential design form, the membrane box has at least one view window. A view window is meaningful at the front side particularly if the membrane box is integrated with its front side into the gas screen. Additionally a view window can be meaningful in the topside so that one can observe the specimens well if the membrane box is taken out of the climate control unit. A view window is meaningful on the lower side if the specimens are supposed to be analyzed with a reverse microscope without being taken out of the germ-proof atmosphere. A membrane box taken out of the climate control unit is purposefully self-supporting and stackable with other membrane boxes of similar type. It is advantageous if the membrane box is adjusted in its shape to the specimen containers to be used. Usually it is cuboid. On the contrary, for the germ-proof storage of bottles cylindrical membrane boxes can be more meaningful. A cylindrical membrane box can also be provided with a screw closure instead of a door. Also an adjustment of the membrane boxes to the shape of the climate control unit is also convenient so that the membrane boxes can be put in and taken out of the climate control unit with accuracy in fitting.

In another variant of the design form the membrane box has a closing device that closes automatically when the membrane box is taken out of the climate control unit. This can be e.g., a flap (shutter) that opens and automatically falls back when something is inserted into or taken out of the climate control unit respectively. For the transport of unfilled membrane boxes it is advantageous if these can be folded together flatly similar to a paper bag or an accordion.

A membrane box is purposefully manufactured out of sterile material. This can be in case of steam sterilization e.g., heat-resistant plastic. Also chemical methods for disinfection are possible after a contamination. In the case of a contamination with dangerous agents, sterilization in an equipment is also thinkable whereby the membrane box is destroyed. During their delivery in the sale process, unused membrane boxes are themselves sterile. They are packed sterilely and folded in a space-saving manner.

For the transport of a filled membrane box it has advantageously a transport container in which the membrane box can be enclosed making it water vapor-tight and gas-tight. Such a transport container has preferentially at least one view window or is at least manufactured in part or completely out of transparent material.

In an advantageous design form the transport container has a device for tempering for longer transports. This can take place through battery-backed systems or simply through a heat saving material with high heat capacity. A simpler variant maintains the temperature alone through thermal isolation.

Also a device for the reception and control of the gas composition in the transport container is purposeful. This happens e.g., by means of a connected transportable gas bottle.

For the reception of the air moisture in the transport container, the latter has a moisture device. This can be a water reservoir in the transport container. In order to avoid the flowing of water in the transport container preferentially a sponge structure soaked with water is used as moisture device. For heating, gas supply and active humidification battery-operated systems are possible that can be controlled via independent control circuits.

Additionally the transport container can have a closable formation.

In a preferential design form the membrane box or the transport container has a reader for transmitting information about specimens. The reader can communicate with an evaluation unit. The information about specimens can be saved on a bar code or magnetic strips. While positioning the specimens into the membrane box or in the transport container this information is recorded by a reader automatically. The reader in turn can communicate with an evaluation unit. For purposes of checking and data recording it is connected e.g., to a PC. This communication can also occur wirelessly e.g., with Bluetooth technology.

For carrying a membrane box from a climate control unit into a transport container with minimum disturbance of the atmosphere in the membrane box the transport container has an opening. This opening can be sealed against the gas screen of a climate control unit thus making it gastight. The transport container also has a closing instrument, which essentially prevents the intrusion of the outside atmosphere into the transport container. The transport container can be fastened to the gas screen of the climate control unit such that the opening of the transport container encloses the front side of the membrane box inserted in the gas screen. The membrane box is then put into the transport container. During this transfer the membrane box can always remain in controlled atmosphere. Similarly the reverse route of transport is also possible. Thereby the membrane box can be created such that the reverse wall of the membrane box is itself gastight and forms the gastight rear wall of the transport container.

In another variant the membrane box is completely inserted in the transport container and behind the membrane box the transport container is closed with a sliding device before the transport container is released from the gas screen.

In the following the invention is explained on the basis of examples of implementation illustrated in the figures.

DESCRIPTION OF THE DRAWINGS

The figures illustrate schematically:

FIG. 5: a side view of a section of a membrane box that can be taken out in accordance with FIG. 4, that can be inserted into a transport container and whose gastight rear wall forms the rear wall of the transport container and FIG. 6: a side view of a section of another version of a membrane box in accordance with FIG. 4 in a transport container that is closed behind the membrane box by a sliding device.

DETAILED DESCRIPTION

Figure 1:
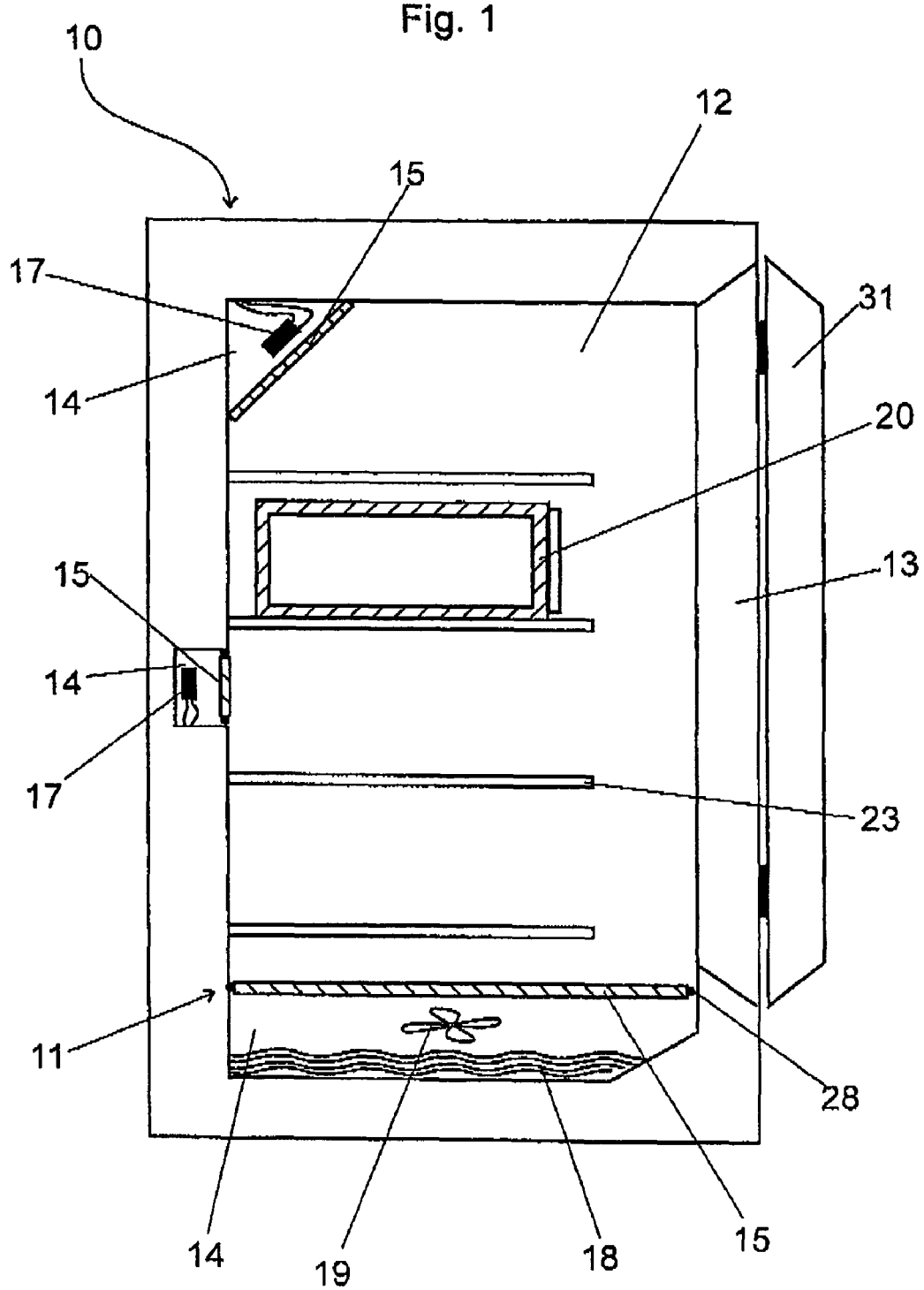
FIG. 1: a side view of a climate control unit in vertical section through the front center with sections separated by membranes.

FIG. 1 illustrates a climate control unit 10 with an interior section 11 that is accessible by a closable access opening 13. The swinging door 31 that closes the interior section 11 is illustrated in side view and in an opened state. In the interior section of the climate control unit are several sections 14 divided by membranes 15. The floor of the interior section is covered by a water bath 18. The water bath is sealed by a membrane 15 stretched on a frame and sealings 28 along the sidewalls of the interior section against the storage space 12. For better diffusion in the interior section 11, the section 14 with the water bath is additionally equipped with a ventilator 19. In the rear wall of the interior section is a recess that is sealed against the storage section 12 by a membrane 15. Inside this separated section 14 is a sensor 17. Another sensor 17 is attached in a section 14 that is separated by a membrane 15. The sensor 17 is attached in the corner between the ceiling and rear wall of the interior section. For storing the specimens the interior section is provided with shelf-like horizontal inserts 23. A closed membrane box 20 is located on an insert. The membrane box 20 separates an additional part of the interior section by a membrane.

Figure 2:
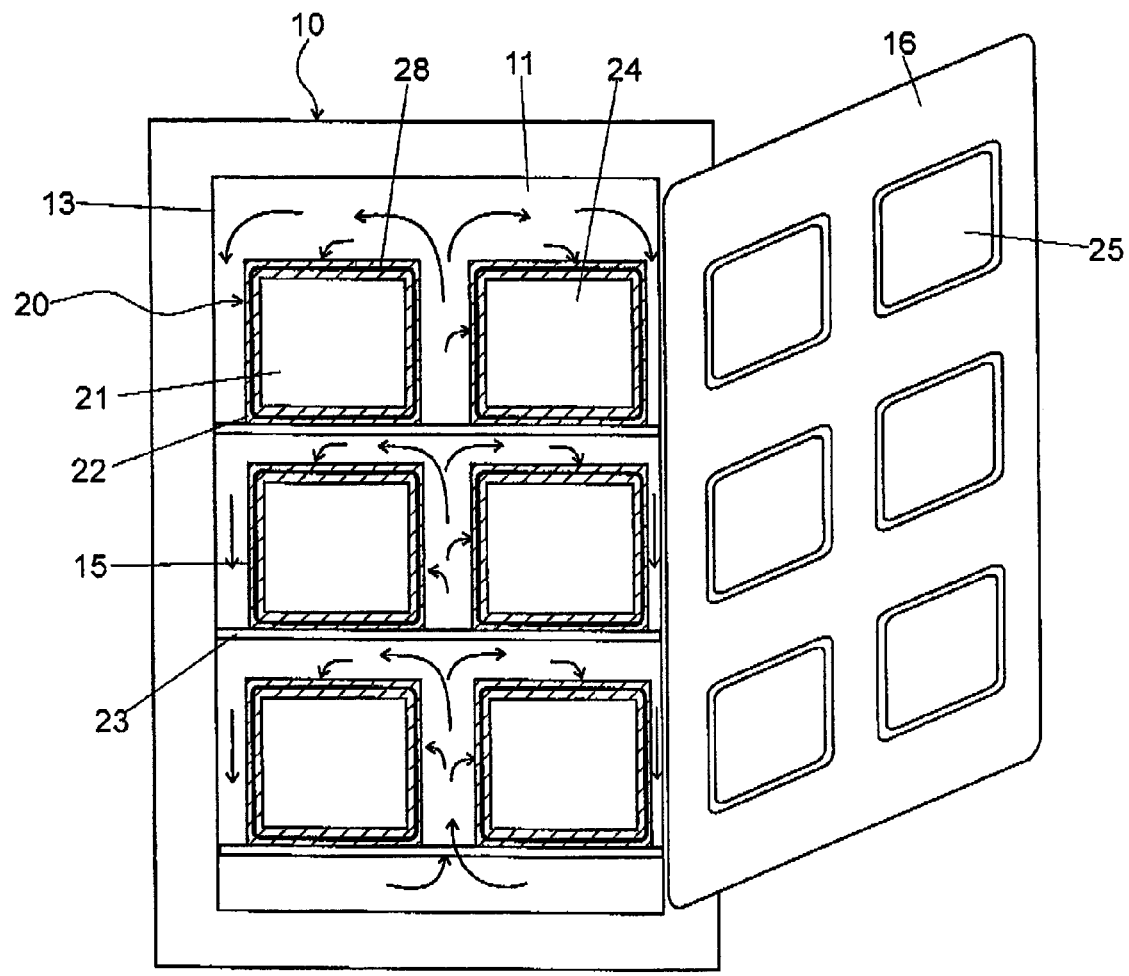
FIG. 2: a front view of the opened front side of a climate control unit with foldable gas screen and membrane boxes that are open to the front and separate doors that are integrated into the gas screen.

In FIG. 2 six such membrane boxes 20 are illustrated in the interior section 11 of a climate control unit. This design variant of membrane boxes 20 is open to the front and equipped with a sealing 28. The membrane boxes are sealed to the front by a gas screen 16 that is illustrated here in an opened state. Every membrane box is accessible by a separate door 25 in the gas screen 16. The membrane boxes 20 do not fill out the entire interior section of the climate control unit 10 so as to enable the diffusion of moist air. The arrows in the illustration illustrate the diffusion. However they do not in any way represent or restrict the actual streaming in the climate control unit.

Figure 3:
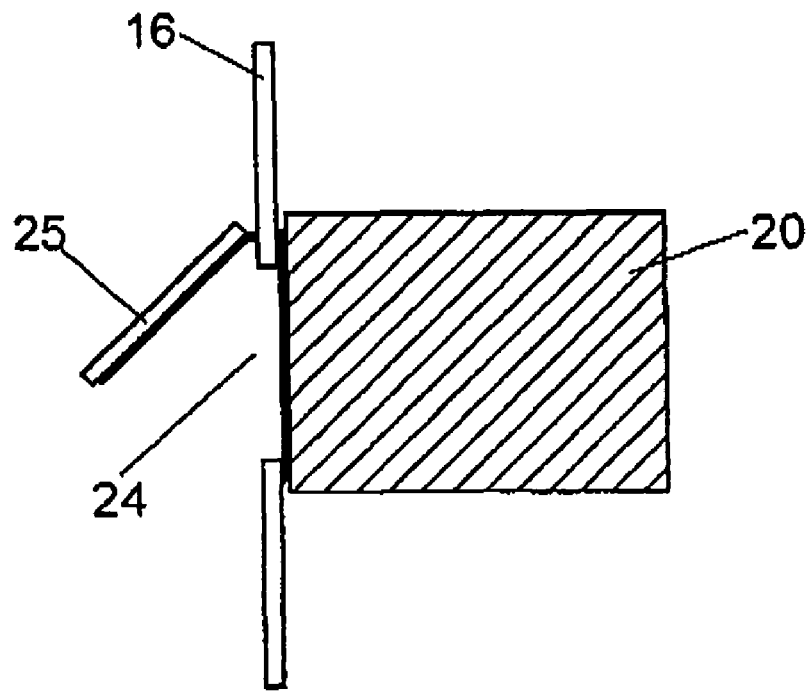
FIG. 3: a top view of a membrane box that is open to the front and is sealed against the gas screen and whose door is attached to the gas screen.

FIG. 3 illustrates the top view of a membrane box 20 as in FIG. 2. The membrane box 20 closes at its opening 24 with a sealing 28 against the gas screen 16. The opening in the gas screen can be closed by a door 25 attached to the gas screen.

Figure 4:
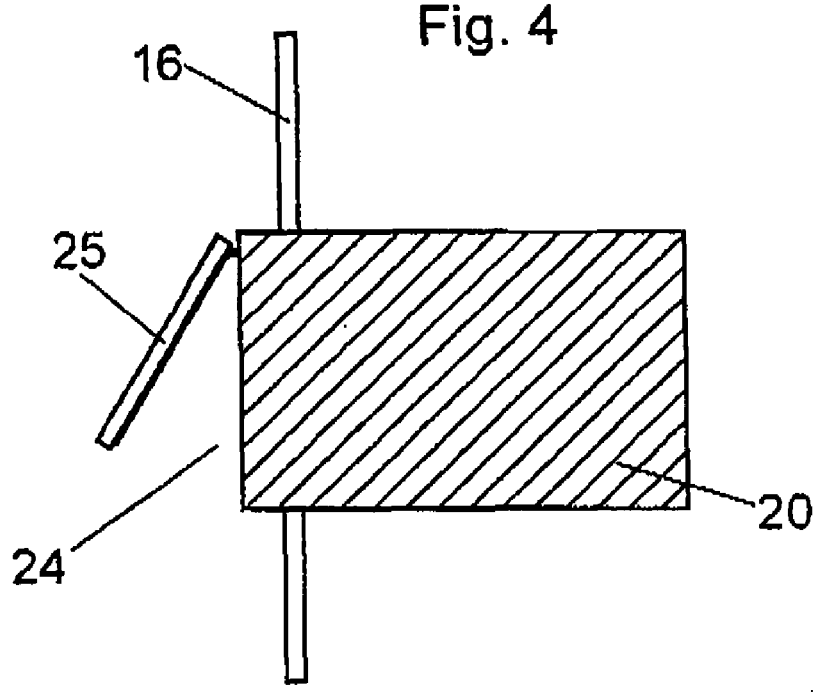
FIG. 4: a top view of another version of a membrane box with a door attached to it that is inserted into the gas screen from the front.

Another version of a membrane box is illustrated in FIG. 4. This membrane box 20 has a door 25 that is itself attached to the membrane box. According to this variant of the design form, the membrane box 20 can be completely taken out of the climate control unit 11 in its closed state. Built in the climate control unit 10 it is inserted from the front into the opening of a gas screen 16.

FIG. 5 illustrates another variant of this design form. The membrane box 20 is inserted halfway into the interior section 11 of the climate control unit and is inserted by a gas screen 16 into a transport container 26. The transport container 26 has a carrying handle and is connected to the gas screen 16 via seals 28. The membrane box 20 has a gastight rear wall 29 that in the inserted state also forms the rear wall of the transport container 26.

FIG. 6 illustrates another variant of a membrane box 20 in a transport container 26. In this illustration the membrane box is completely inserted into the transport container. The transport container 26 is connected via sealings against the gas screen 16 of the climate control unit. The transport container 26 is closed with a sliding device 30 while it is still connected to the gas screen 16 and the atmosphere of the climate control unit 10. The transport container 26 is released from the climate control unit only when it 26 is closed.

The invention claimed is:
1. A climate control unit, comprising:
a door; and
a housing defining a climate-controlled interior section, the interior section being accessible by an access opening that is closable by the door, the interior section including:
a water bath;
a plurality of individual sections, and
at least one membrane separating the interior section into at least two of the individual sections, at least one of the two individual sections defining a germ-proof separated space, the membrane being permeable for water vapor and gas and impermeable for microorganisms,
wherein the water bath and a ventilator are located in the germ-proof separated space.

2. The climate control unit in accordance with claim 1 wherein a thermal bridge is located between the germ-proof separated space and a second of the at least two individual sections of the interior section, the thermal bridge being configured to condense out excessive water vapor in the second of the at least two individual sections of the interior section.

3. A climate control unit, comprising:
a door;
a housing defining a climate-controlled interior section, the interior section being accessible by an access opening that is closable by the door, the interior section including:
a plurality of individual sections,
at least one membrane separating the interior section into at least two of the individual sections, at least one of the two individual sections defining a germ-proof separated space, the membrane being permeable for water vapor and gas and impermeable for microorganisms, and
at least one membrane box, the membrane box enclosing, with exterior walls, at least one storage cell for specimens, the membrane box being configured to make the storage cell germ-proof, whereby at least one sub area of these exterior walls is formed out of a membrane that is permeable for water vapor and gas but impermeable for microorganisms.

4. The climate control unit in accordance with claim 3 further comprising a fixing device to which the membrane box is releasably fastened in the interior section of the climate control unit.

5. A climate control unit, comprising:
a door;
a housing defining an interior, the interior being accessible by an access opening that is closable by the door, the interior including:
a plurality of individual sections,
at least one membrane separating the interior into at least two sections, to separate one of the at least two sections to form a germ-proof separated space, the membrane being permeable for water vapor and gas and impermeable for microorganisms;
a gas screen arranged between the access opening and the interior of the climate control unit, whereby the gas screen closes the interior of the climate control unit; and
a membrane box releasably fastened to the gas screen.

6. A climate control unit comprising:
a door;
a housing defining an interior, the interior being accessible by an access opening that is closable by the door, the interior including:
a plurality of individual sections, and
at least one membrane separating the interior into at least two sections, to separate one of the at least two sections to form a germ-proof separated space, the membrane being permeable for water vapor and gas and impermeable for microorganisms;
at least one membrane box enclosing, with exterior walls, at least one storage cell for specimens, the membrane box being configured to make the storage cell germ-proof, whereby at least one sub area of those exterior walls is formed out of a membrane that is permeable for water vapor and gas but impermeable for microorganisms, the membrane box having-at least one load opening that is releasably closable with a closing device and is therefore substantially germ-proof, wherein the closing device is a door.

7. The climate control unit in accordance with claim 6 further comprising a gas screen arranged between the access opening and the interior of the climate control unit, the door being integrated into the gas screen and the membrane box being sealed against the gas screen.

8. The climate control unit in accordance with claim 6 wherein the closing device is fastened to the membrane box and sealed against it.

9. The climate control unit in accordance with claim 8 wherein the membrane box can be taken out of the climate control unit together with the door.

10. The climate control unit in accordance with claim 9 further comprising a substitute closing device that closes an aperture resulting by taking out a membrane box.

11. The climate control unit in accordance with claim 9 wherein the membrane box is enclosed by walls, thus germ-free, from which at least one sub area is formed by a membrane that is permeable for water vapor and gas but impermeable for microorganisms and that it has at least one load opening that can be closed by a closing device particularly a door, so as to be releasable and germ-proof.

12. The climate control unit in accordance with claim 11 wherein the membrane has pores with a maximum pore size of 0.5 μm.

13. The climate control unit in accordance with claim 11 wherein the membrane box comprises at least one view window.

14. The climate control unit in accordance with claim 11 wherein the membrane box comprises a closing device that closes automatically when it is taken out of the climate control unit.

15. The climate control unit in accordance with claim 11 wherein the membrane box can be folded together flatly for transport.

16. The climate control unit in accordance with claim 11 wherein the membrane box is manufactured out of a sterile material.

17. The climate control unit in accordance with claim 11 wherein the membrane box comprises a transport container in which the membrane box can be enclosed in a water vapor-tight and gastight manner.

18. The climate control unit in accordance with claim 17 wherein the transport container is manufactured at least in part out of transparent material.

19. The climate control unit in accordance with claim 17 wherein the transport container has a device for tempering.

20. The climate control unit in accordance with claim 17, wherein a transportable gas bottle is connected to the transport container to control the gas composition therein.

21. The climate control unit in accordance with claim 17 wherein the transport container has a moisture device with which the air moisture in the interior can be regulated.

22. The climate control unit in accordance with claim 21 wherein the moisture device has at least one sponge structure soaked with water.

23. The climate control unit in accordance with claim 22 wherein the transport container has a reader for transmitting information about specimens, wherein the reader can communicate with an evaluation unit.

24. The climate control unit in accordance with claim 23 wherein the reading device and the evaluation unit have means for wireless communication.

25. The climate control unit in accordance with claim 24 wherein the transport container has an opening that is sealed against the gas screen of the climate control unit and thus is gastight, and that it has in addition a closing instrument that essentially prevents the intrusion of the outside atmosphere.

26. The climate control unit in accordance with claim 25 wherein the membrane box comprises a gastight rear wall that is sealed against the transport container making it gastight and that forms the rear wall of the transport container.

27. The climate control unit in accordance with claim 26 wherein the transport container has a sliding device in the area of its opening with which it can be closed in a gastight manner while the opening is sealed in a gastight manner against the gas screen of a climate control unit.

* * * * *

UNITED STATES PATENT AND TRADEMARK OFFICE
CERTIFICATE OF CORRECTION

| | | |
|---|---|---|
| PATENT NO. | : 7,867,762 B2 | |
| APPLICATION NO. | : 11/029630 | |
| DATED | : January 11, 2011 | |
| INVENTOR(S) | : Hermann Stahl et al. | |

It is certified that error appears in the above-identified patent and that said Letters Patent is hereby corrected as shown below:

On the Cover Page, column 2, add "(74) Attorney, Agent, or Firm – Wood, Herron & Evans, LLP".

In column 2, line 19, change "Thus germ-proof separated section is formed." to --Thus a germ-proof separated section is formed.--.

In claim 6, column 9, line 2, change "the membrane box having-at least" to --the membrane box having at least--.

Signed and Sealed this
Twenty-fourth Day of May, 2011

David J. Kappos
*Director of the United States Patent and Trademark Office*